United States Patent [19]
Cravador et al.

[11] Patent Number: 5,218,102
[45] Date of Patent: Jun. 8, 1993

[54] NUCLEIC ACID PROBE CONTAINING A TERMINAL CARBAMYL LINKING NON-RADIOACTIVE LABELING AND PREPARATING PROCESSES

[75] Inventors: Alfredo Cravador, Rhode-St-Genese; Marie-Joëlle de Vos-Pierreux, Feluy; Alex Bollen, Itterbeek, all of Belgium

[73] Assignee: Improbio, Nivelles, Belgium

[21] Appl. No.: 315,348

[22] Filed: Feb. 23, 1989

[30] Foreign Application Priority Data

Feb. 24, 1988 [FR] France .................... 88 02228

[51] Int. Cl.⁵ .................... C07H 21/00; C07H 19/00; C12Q 1/68
[52] U.S. Cl. .................... 536/24.3; 435/6; 435/91; 435/810; 436/501; 536/25.32; 536/25.31; 536/26.6; 536/25.33; 536/26.12; 536/26.71; 536/26.72; 536/26.8; 935/78; 935/88
[58] Field of Search .................... 435/6, 91, 810; 436/501; 536/27, 26, 28, 29; 935/78, 88

[56] References Cited

U.S. PATENT DOCUMENTS 4,711,955 12/1987 Ward et al. .................... 536/29
4,775,619 10/1988 Urdea .................... 435/6

FOREIGN PATENT DOCUMENTS

| | | |
|---|---|---|
| 0063879 | 11/1982 | European Pat. Off. |
| 0131830 | 1/1985 | European Pat. Off. |
| 0143059 | 5/1985 | European Pat. Off. |
| 0230363 | 7/1987 | European Pat. Off. |
| 0244860 | 11/1987 | European Pat. Off. |
| WO86/00074 | 1/1986 | PCT Int'l Appl. |
| WO86/05518 | 9/1986 | PCT Int'l Appl. |

OTHER PUBLICATIONS

Chu et al. (1983) Nuc. Acids Res., vol. 11, No. 8, pp. 6513-6529.

(List continued on next page.)

*Primary Examiner*—Amelia Burgess Yarbrough
*Assistant Examiner*—Ardin H. Marschel
*Attorney, Agent, or Firm*—Cooley, Godward, Castro, Huddleson & Tatum

[57] ABSTRACT

The subject of the present invention is a nucleic acid probe containing a nucleic acid sequence, wherein the said sequence is linked at its 5' end, via a divalent bifunctional chemical "arm" L, to a "labeling component" M, M being a synthetic or natural molecule which is directly or indirectly detectable in a non-isotopic manner, according to the formula I:

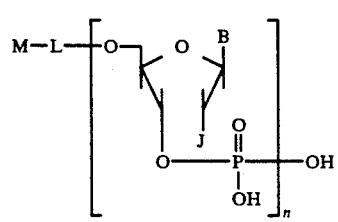

in which
J = H or OH
n denotes the number of nucleotides from 1 to 100,000
B is a purine or pyrimidine nucleic acid base, which varies according to the nucleotide, as appropriate.

The subject of the invention is also a process for preparing such probes, employing an intermediate compound consisting of a nucleotide synthon of formula IV

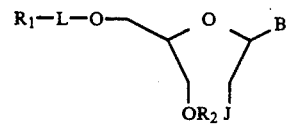

in which
J, B, L and $R_1$ have the meanings given above, B optionally being protected,
$R_2$ denotes H or any phosphorylated group, optionally protected, suited to the introduction of the compound of formula IV at the 5' end of another nucleotide, for a given type of internucleotide-assembling synthesis.

21 Claims, 1 Drawing Sheet

OTHER PUBLICATIONS

Renz (1983) Embo J., vol. 2, No. 6, pp. 817–822.
Renz et al. (1984) Nuc. Acids Res., vol. 12, No. 8, pp. 3435–3444.
Ruth et al., *DNA* (1985) 4(1):93.
E. M. Southern in *J. Mol. Biol.* (1975) 98:503–517.
McBride and Caruthers, *Tetrahedron Letters* (1983) 24(3):245–248.
Saiki et al., *Science* (1988) 239:487–491.
Sinha et al., *Nucleic Acids Research* (1984) 12(11):4539–4557.

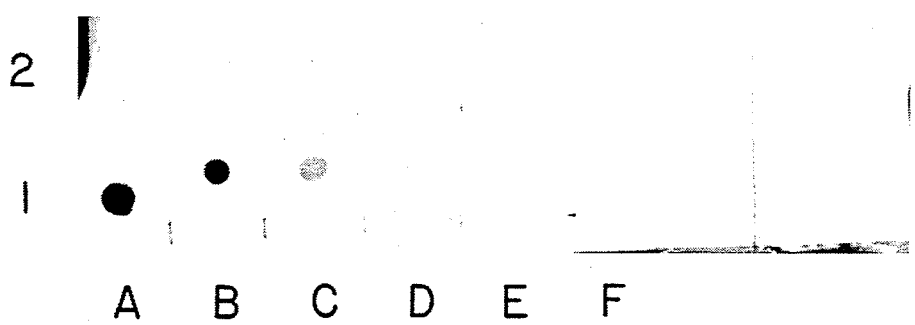

NUCLEIC ACID PROBE CONTAINING A TERMINAL CARBAMYL LINKING NON-RADIOACTIVE LABELING AND PREPARATING PROCESSES

The present invention relates to non-reactive nucleic acid probes, and to chemically modified nucleotide compounds which are useful, in particular, in the synthesis of the said probes.

The use of nucleic acid probes for detecting and diagnosing hereditary genetic diseases, oncogenes and viral, bacterial or parasitic diseases is tending to become widespread, and finds applications in the clinical, veterinary and plant fields. These probes are generally single-stranded DNA or RNA sequences capable, under certain experimental conditions, of finding their complementary sequences and of hybridizing with them to form stable duplexes. The classical method of detection of DNA/DNA or DNA/RNA hybrids- employs radioactive labeling; in general, the DNA is labeled with the radioisotope $^{32}P$. When these probes are radioactive, it is then possible to detect the hybridization by counting or autoradiography. The use of radioisotopes has, however, many drawbacks:

a) loss of the specific activity due to the relatively short life of the isotope;

b) practical problems of application, which oblige protective measures to be taken against radiation and complicate the use of these probes by nonexperts;

c) the necessarily very high cost as a result of these constraints.

Recently, probes which are "cold", since they do not comprise radioactive elements, have hence been developed. They employ detection techniques mainly using enzyme systems, for example alkaline phosphatase or peroxidase. These enzymes react with a colorless and soluble chromogenic substrate, which gives a precipitated colored product thereby permitting a rapid visualization of the hybridization.

Many other systems may be employed, which are recalled, in particular, in Patent Applications EP 63,879 and EP 143,059, to which reference may be made in order to gain the best understanding of the present patent application. For example, the detection of the hybridized probe may be carried out by fluoresence techniques using fluorescein.

The techniques which have been developed may be classified in two large categories:

1) The first consists in coupling the probe to a directly detectable component. A direct detection of the hybrid is obtained, for example by covalent coupling of an enzyme to the probe. Thus, in Application EP 120,376, polyethylenimine has been used for coupling peroxidase to DNA in the presence of glutaraldehyde. Or alternatively, alkaline phosphatase has been bound on the 5-carbon of thymine via an aminated functional arm through an amide bond with a carboxyl group of the enzyme.

2) The second category consists in the indirect detection of the nucleic acid hybrid. Use is made of intermediate substances which recognize units bound to the probe. The systems in question are mainly based on the interaction between a biotinylated probe and avidin, the avidin being most often conjugated to an enzyme. This system is based on the great affinity between biotin and avidin. Streptavidin is nowadays preferably used in place of avidin. The streptavidin/biotin system currently proposed necessitates, however, the incorporation of modified nucleotides, linked to a biotin, into the nucleic acid probe, by means of a nick translation, a technique also known as cut displacement. This nick translation is a relatively complex technique, in which the use of enzymes such as $E.$ $coli$ polymerase I and diluted deoxyribonuclease I, is employed.

The indirect detection techniques proposed can also include the use of antibodies. The probe can be a carrier of haptenic groups linked to first antihapten antibodies, which are themselves detected by other antibodies directed towards the first antibodies, these other antibodies being labeled by application of a non-radioactive technique.

The major drawback of the proposed techniques, whether they depend on direct or indirect detection, resides in the chemical modification of the nucleotides of the probe which they involve.

Oligodeoxyribonucleotides bearing chemical groups permitting coupling with a variety of reagents have been described in the literature. The introduction of these groups is generally carried out on one or more of its bases along the oligonucleotide chain.

Chemical modifications in the bases have the disadvantage of interfering with base pairing during the process of hybridization of the oligonucleotide with homologous sequences.

In addition and above all, none of the direct or indirect detection techniques proposed hitherto propose labeled probes which are capable of being synthesized completely, that is to say including the binding of the labeling component for direct or indirect detection, under traditional conditions of manual or automatic synthesis of nucleic acids, in particular on a solid support.

The object of the present invention is hence to obtain nucleic acid probes:

affording good hybridization with the complementary target sequences, permitting direct or indirect detection by nonradioactive methods and with as low a detection threshold as possible, and which, in addition, are readily synthesizable, that is to say suited to automatic or manual nucleic acid synthesis, in particular on a solid support.

To this end, the present invention consists in preparing mixed molecules composed of an oligonucleotide or oligodeoxynucleotide portion and another portion consisting of a molecular group possessing properties permitting the ready and rapid detection of complementary nucleic acid targets by non-radioactive methods. The nucleotide portion, which consists of a defined nucleic acid sequence homologous with a target complementary fragment, contributes the energy of stabilization and provides for hybridization with the DNA or RNA molecule which it is desired to detect. The portion which supplies the reactivity enabling the hybrid to be detected directly or indirectly, also referred to as the "labeling component", is coupled at a 5' end of the nucleic acid sequence referred to above. This coupling is carried out via a covalent chemical link, also referred to as an "arm", which is designed to avoid steric hindrance between the labeling component and the nucleic acid sequence of the probe on the one hand, and possible interference in the hybridization of the probe with the target sequence on the other hand.

The subject of the present invention is, in effect, a nucleic acid probe containing a DNA or RNA nucleic acid sequence (S), wherein the said sequence (S) is linked at its 5' end, via a divalent chemical arm (L), with a labeling component (M), M being a synthetic or natural molecule which is directly or indirectly detectable in a non-isotopic manner, according to the formula S-L-M.

The chemical modification of the terminal nucleotide of the nucleic acid sequence for its binding to the labeling component is carried out at the 5' position, such that the formula I may be split up in the following manner. If S denotes a sequence of n nucleic acids

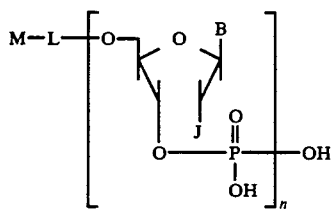

in which
J=H or OH
n denotes the number of nucleotides, from 1 to 100,000
B is a purine or pyrimidine nucleic acid base, which varies according to the nucleotide.

It will be recalled that nucleic acids are nucleotide polymers; ribonucleotides in the case of RNA, deoxyribonucleotides in the case of DNA. The monomers, that is to say the nucleotides, consist, it may be recalled, in the case of RNA, of phosphoric acid, a monosaccharide containing 5 carbon atoms, ribose (J=OH) and one of the four fundamental bases adenine, guanine, cytosine, uridine. So-called minor bases or nucleosides, such as methylated or hydroxylated bases, dihydrouracil and pseudouridine, are encountered more rarely. In the case of DNAs, the deoxyribonucleotide monosaccharide is D-2-deoxyribose (J=H) and the four main bases are adenine, guanine, cytosine and thymine; in rare cases, cytosine is replaced by methylcytosine or hydroxymethylcytosine. One of the essential characteristics of polynucleotides is the 3':5' phosphodiester internucleotide bond.

The synthesis of the compound I can hence be carried out by traditional internucleotide synthesis with elongation at the 5' end of the terminal nucleotide. To this end, the covalent chemical link between the arm and the nucleic acid sequence at the 5' position must be stable, in particular under the conditions of cleavage of the oligonucleotide or oligodeoxynucleotide from the solid support, as appropriate, and under the conditions of the deprotection on the bases and phosphates which are involved in internucleotide syntheses.

Thus, in a preferred embodiment according to the present invention, the chemical arm consists of a bifunctional divalent chemical residue capable of creating a carbamate link with the 5'-hydroxyl group of the nucleic acid sequence, a chemical residue, in particular, of formula II:

$$-L'-\overset{O}{\underset{\|}{C}}-$$

where —L'— is a residue aminated at both of its ends.
More especially, L denotes a residue

in which Alk denotes a straight or branched alkyl chain having 2 to 20 carbon atoms. The arm L of formula II produces a carbamate link which is stable, under the cleavage and deprotection conditions referred to above, with the 5' (OH) end of the nucleic acid sequence.

When L is of the formula III

Alk preferably denotes a straight chain having 2 to 12 carbon atoms.

As a further preference, Alk denotes a $-(CH_2)_6-$ group.

The labeling component M can denote a traditional directly detectable molecule. In particular, M can be chosen from enzymes suited to visualization by a chromogenic substrate, among which special mention may be made of microperoxidase and alkaline phosphatase.

According to the present invention, M can, however, advantageously denote a macromolecule to which several directly detectable groups such as enzymes or fluorescent molecules, such as fluorescein, are bound. In this case, M can denote a synthetic polymer such as polyethylenimine to which such groups, for example enzymes or fluorescent molecules, are bound.

Polyfluoresceinylpolyethylenimine may be mentioned more especially according to the present invention. This type of compound results in an amplification of the labeling, and hence a fall in the detection threshold.

M can also denote a traditional indirectly detectable molecule, such as biotin or one of its derivatives bearing a hydrocarbon chain through which the link with L is made and which contributes to an increase in the distance from the oligonucleotide, or alternatively a macromolecule such as an antibody. According to the present invention, M can advantageously denote a macromolecule to which several indirectly detectable groups are bound, for example a polybiotinylated synthetic polymer such as polybiotinyl polyethylenimine.

The subject of the present invention is hence also, by way of intermediate product which is useful, in particular, as a component for labeling a nucleic acid probe, a synthetic polymer, in particular a polyamine such as polyethylenimine, to which several directly detectable groups, for example fluorescent molecules, are bound, in particular polyfluoresceinylpolyethylenimine as a means of direct detection, or polybiotinylpolyethylenimine as a means of indirect detection.

The subject of the present invention is, likewise, a process for preparing a probe of formula I, comprising:
a) the synthesis of a nucleic acid sequence of formula Ia:

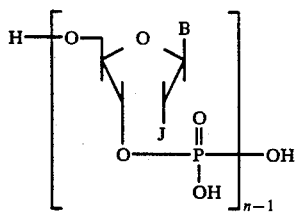

in particular by any known manual or automatic method of internucleotide-assembling synthesis preferably on a solid support, wherein the said sequence is subjected, preferably by one and the same synthetic method, in particular on a solid support, to b) an extension at its free 5' (OH) end, onto the 3' (OH) end of a nucleotide or deoxynucleotide synthon, the latter being protected at the 3' position by a phosphorylated group suited to the type of synthesis employed, and bearing at the 5' position a chemical arm L protected at its free end by a group $R_1$, of formula IV

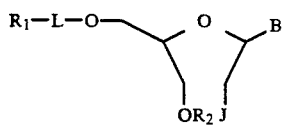

in which

J, B, L and $R_1$ have the meanings given above, B optionally being protected, $R_2$ denotes H or any phosphorylated group, optionally protected, suited to the introduction of the compound of formula IV at the 5' end of another nucleotide for a given type of internucleotide-assembling synthesis, to give the compound of formula Ib

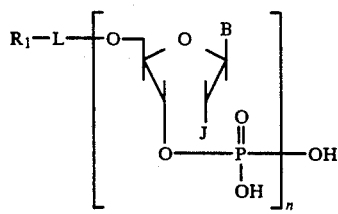

the group $R_1$, after activation, in particular by means of a bifunctional group such as a diepoxide, establishes c) the coupling with the molecule, the "labeling component" M.

When the "labeling component" M consists of a biotinylated or fluoresceinylated chemical polymer, the said chemical polymer is labeled under non-saturating conditions, with the result that it retains nucleophilic groups so that the labeled polymers couple to the oligonucleotide bearing the chemical "arm".

When the synthesis of the probe of formula I is carried out entirely on a solid support, the coupling reaction of the stage c) may be performed when the substrate, the product of the stages a) and b), is still bound to the solid support, or alternatively after cleavage, when the stability of the bond with the molecule M is insufficient under the cleavage conditions.

When M denotes a macromolecule to which one or more directly or indirectly detectable groups are bound, the binding of the said groups to the macromolecule can take place before or after the coupling of the latter onto the substrate, the product of the stages a) and b).

The activation for the coupling of the stage c) can take place with a diepoxide, as noted, but also with diisocyanatohexane or suberic acid N-hydroxysuccinimide diester.

By way of an intermediate product which is useful, in particular, for the synthesis of a probe of formula I, according to the above process, the subject of the present invention is also a synthetic nucleotide compound, also referred to as a synthon, which is represented by the formula IV:

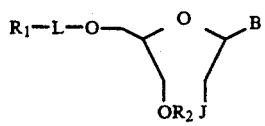

in which:

J=H or OH

B denotes a nucleic acid base, optionally protected

L is a divalent bifunctional chemical arm $R_1$ is a protective group for the free terminal group of L $R_2$ denotes H or any phosphorylated group, optionally protected, suited to the introduction of the synthon at the 5' end of another nucleotide for a given type of internucleotide-assembling synthesis.

$R_2$ can denote, by way of illustration in the case of phosphoramide synthesis on a solid support, the cyanoethyldiisopropylphosphoramidite group of formula V

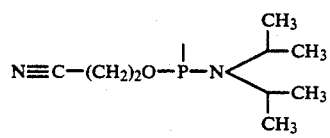

This phosphorylation at the 3' (OH) position is obviously not limiting; it is possible, in particular, to envisage synthesis of a phosphate triester or diester in the case of phosphotri- or diester synthesis.

Preferably, the bifunctional chemical arm L can be represented by a residue of formula

in which L' is a diaminated residue.

When L denotes a residue

where L' is a diaminated residue, for example when L is of the formula

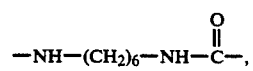

there may be mentioned as a suitable protective group $R_1$ for the terminal amino group, still by way of illustration, the diphenylisopropyloxycarbonyl group, which is labile under acid conditions, of formula VI:

A product according to the invention corresponds to the formula VII

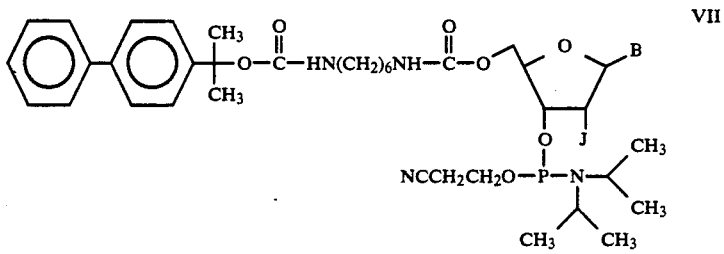

in which B and J have the meanings given above.

It is appropriate to emphasize that the compounds of formula IV are applied by way of illustration to the labeling of a nucleic acid probe, and that other applications of them can hence be made.

It is possible to envisage, for example, binding a nucleic acid sequence to a solid support using such compounds.

The subject of the invention is, in addition, a process for preparing a compound of formula IV, comprising the following stages:

1) The selective protection of the hydroxyl group at the 3' position of the nucleoside of formula VIII

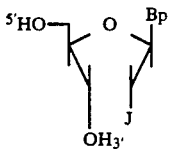

in which Bp is a protected nucleic acid base and J=H or OH.

2) The selective activation of the hydroxyl group at the 5' position.

3) A coupling reaction at the 5' position to give the singly protected chemical "arm" of formula $R_1$—L, where L has the meaning given above.

4) Deprotection of the hydroxyl group at the 3' position, and optionally

5) Phosphorylation with a reagent which permits solid phase coupling of the nucleotide thus modified at the 3' position, coupling to the 5' end of another nucleotide by a given type of internucleotide-assembling synthesis.

When the arm L can be represented by the formula

in which L' denotes a diaminated residue, the selective activation of the 5'—OH will preferably be carried out with the carbonyldiimidazole (CDI) group. The coupling reaction 3) above will be carried out with the diaminated residue singly protected on a terminal amine, of formula $R_1$—L', $R_1$ preferably denoting a diphenylisopropyloxycarbonyl group.

The selective protection of the hydroxyl group at the 3' position will preferably be carried out with the dimethyl-tert-butylsilyl group, this silyl group being stable during the activation reaction 2 with CDI. Moreover, this group is well suited, generally speaking, to the subsequent stages of the synthetic pathway.

When the selective protection in the stage 1) of the 3'—OH group is carried out with the silyl group mentioned above, the deprotection in the stage 4) can be carried out with tetrabutylammonium fluoride.

In the stage 5), the phosphorylation, in the case of phosphoramidite synthesis, may be carried out with diisopropylaminocyanoethoxychlorophosphine of formula IX

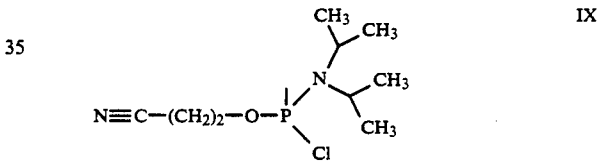

The stage 1 of the above process can also be split up in the following manner:

1a)—Selective protection of the 5'—OH end of the nucleoside of formula VIII, this protection preferably being carried out with dimethoxytrityl (DMT), which is labile at acid pH.

1b)—Protection of the 3'—OH of the compound of formula VIII with a group which is labile under mild and neutral conditions, this protection preferably being carried out with a dimethyltert-butylsilyl group; this group being stable during the deprotection reaction 1c) and activation reaction 3).

1c)—Selective deprotection of the DMT to liberate the 5'—OH.

Other characteristics and advantages of the present invention will become apparent in the light of the examples which follow. In Example IV, reference is made to FIG. 1, which shows the visualization of the hybridization of a probe according to the invention for the DNA of the $HPV_{16}$ virus.

BRIEF DESCRIPTION OF THE FIGURE

FIG. 1 shows the visualization of the hybridization of HPV16 target DNA (Row 1) and HPV18 target DNA (Row 2) to a polybiotinylated DNA probe for HPV16 as described in Example IV. The target DNA amounts for spots A-F correspond to 5 μg, 1 μg, 0.1 μg, 10 ng, 1 ng, 0.1 ng, respectively.

EXAMPLE 1

Preparation of the derivative 5'-[2-[4-biphenylyl)propyl-2-oxycarbonylamido-6-hexylamidocarboxy]thymidine 3'-O-(2-cyanoethyl-N,N-diisooropylphosohoramidite)

The derivative 5'-[2-(4-biphenylyl)propyl-2-carbonylamido-6-hexylamidocarboxy]thymidine 3'-O-(2-cyanoethyl-N,N-diisopropylphosphoramidite) corresponds to the formula:

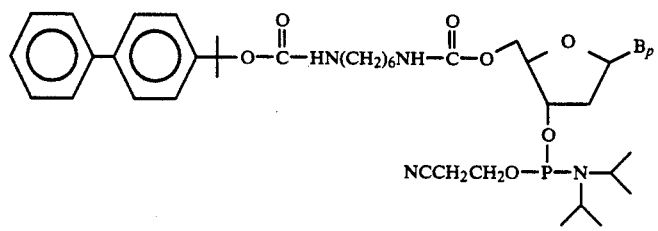

in which $B_P$ denotes the protected thymine base.

The approach followed has as its objective the preparation of a nucleotide synthon bearing, on the one hand the chemical groups which enable it to be introduced into an oligodeoxyribonucleotide during the final elongation cycle under the customary conditions of automatic synthesis, and on the other hand the carboxyalkylamino chain needed for coupling the DNA molecule with a "labeling component" M. This synthon has the advantage of providing the user with a tool permitting the synthesis of a DNA molecule which can be coupled, without departing from the routine of automatic or manual synthesis.

The cyanoethyldiisopropylphosphoramidite group is suited to a phosphoramidite synthesis.

A carbamate link links the 5'—OH group of the nucleotide to hexanediamine, the amino end of which is protected by diphenylisopropyloxycarbonyl, which is labile under acid conditions.

This nucleotide synthon is protected and provided with suitable reactive groups enabling them to be introduced in the solid phase at the 5' end of any synthetic oligodeoxynucleotide, in as much as the carbamate link is stable:

1) under the conditions of removal of the protective groups present on the bases and the phosphates, and
2) under the conditions of cleavage of the oligodeoxynucleotide from the solid support.

A first reaction pathway is shown in Scheme 1 below, which comprises the following stages:

I) selective protection of the 5'—OH with dimethoxytrityl (DMT), which is labile at acid pH II) protection of the 3'—OH with the levulinic group, which is labile in the presence of hydrazine III) selective deprotection of the DMT to liberate the 5'—OH IV) activation of 5'—OH with carbonyldiimidazole V) reaction with hexylenediamine, yielding a stable carbamate link and an amino group at one end VI) protection of the amine with diphenylisopropyloxycarbonyl, which is labile in the presence of acid VII) selective deprotection of the levulinic group with hydrazine to liberate the 3'—OH VIII) phosphorylation at the 3'—OH position. The example of phosphoramidite shown in the scheme is not limiting; it is also possible to envisage the synthesis of a phosphate triester or diester or a phosphonate.

SCHEME 1
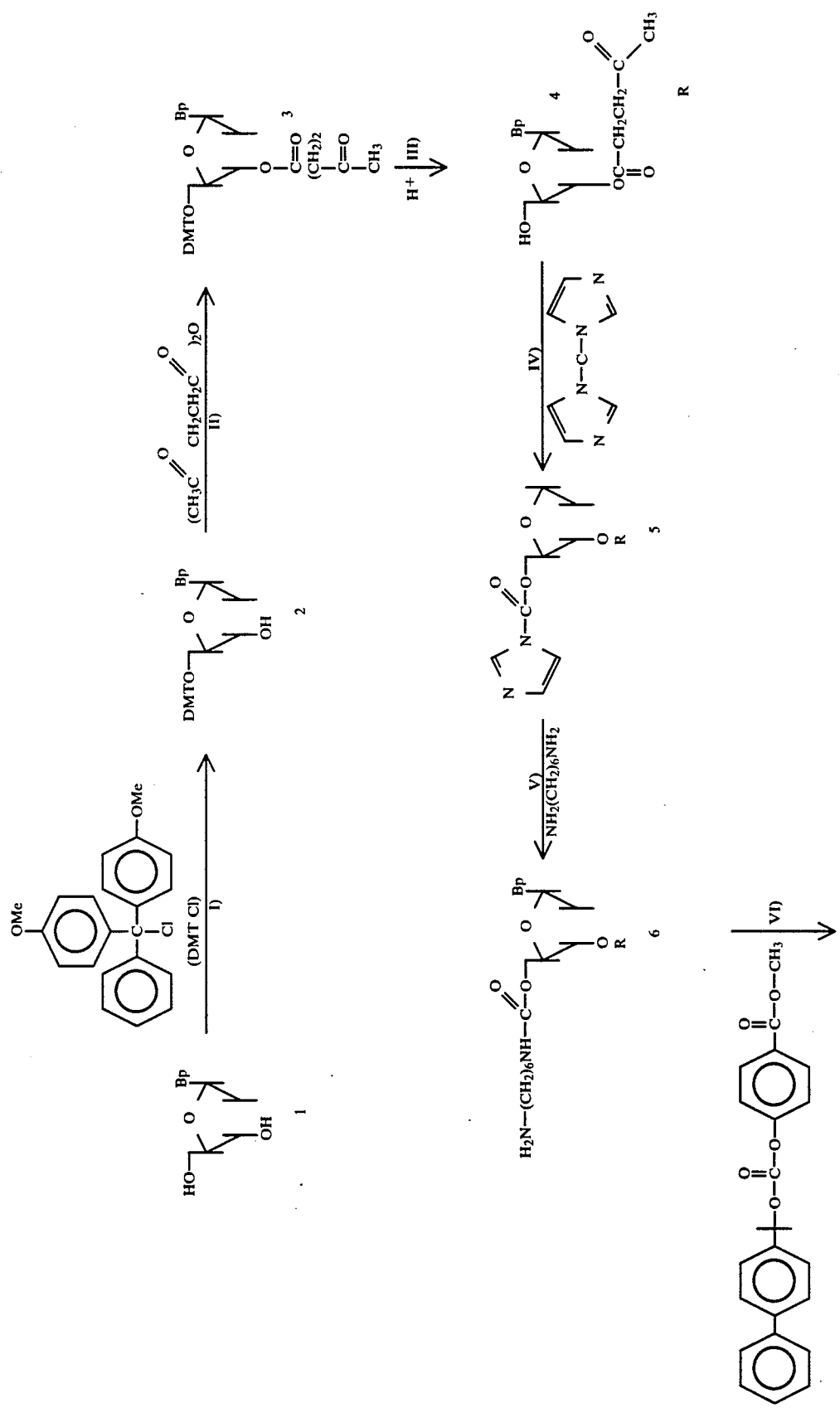

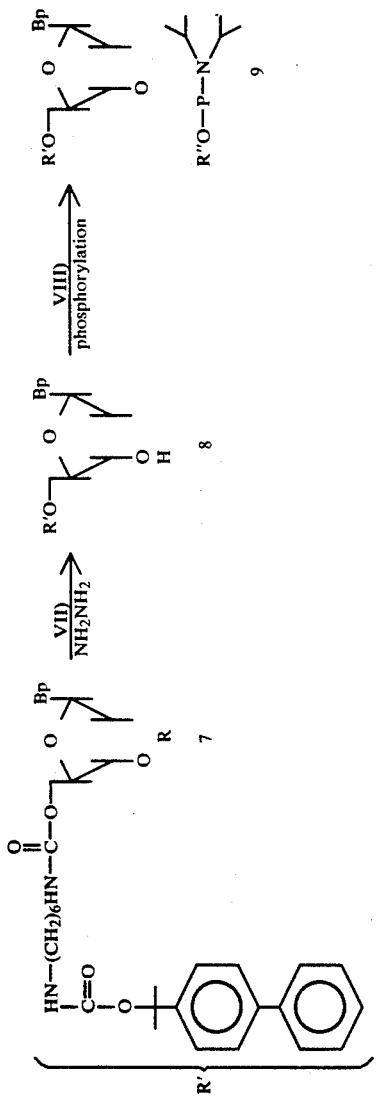

The reaction pathway shown in Scheme 1 is advantageously modified in Scheme 2 below, as a result of the problems caused by the levulinic group during the activation of the hydroxyl group at the 5' position with carbonyldiimidazole (CDI). Although perfectly stable under the reaction conditions used, the derivative 4 (Scheme 1) requires an at least twofold excess of CDI. Since the activated product 5 (Scheme 1) cannot be isolated, the excess CDI pointlessly consumes a molar equivalent of the amino derivative and complicates the purification.

In the reaction pathway shown in Scheme 2 below, the levulinic group has been replaced by a dimethyl-tert-butylsilyl group, which can also be removed under mild and neutral conditions and successfully reproduces the reaction conditions of substitution with 3'-O-dimethyl-tert-butylsilyl-5'-O-(imidazolylcarbonyl)-thymidine (12; Scheme 2), prepared from the derivative 11 (Scheme 2) by reaction of its 5'—OH group with carbonyldiimidazole.

The silyl group does not interfere with the activation reaction with CDI, and is very well suited to the subsequent stages of the synthetic pathway, which was followed as described in Scheme 2.

The substitution reaction with 1,6-diaminohexane is relatively complex on account of the bifunctional nature of the nucleophilic derivative. In contrast, 1-aminohexane under the same conditions gives a straight-forward reaction. To simplify this substitution reaction we hence studied the reactivity of hexanediamine with respect to 2-(4-biphenylyl-)prop-2-yl 4-methoxycarbonylphenyl carbonate (10, Scheme 2) for the purpose of obtaining the protection of a single amino group. The singly protected derivative 13 (Scheme 2) could be isolated in a yield of more than 90%. This monofunctional reagent reacts efficiently with the 3'-O-silylated 5'-O-(imidazolylcarbonyl)thymidine.

The fully protected derivative 14 (Scheme 2) was hence obtained by reaction of the singly protected hexanediamine 13 (Scheme 2) with the compound 12 (Scheme 2) activated at the 5' position by the carbonylimidazole group. Deprotection of 14 with tetrabutylammonium fluoride enables the hydroxyl group at the 3' position to be liberated and access to be gained to the derivative 8 (Scheme 2). The phosphorylation of 8 with diisopropylaminocyanoethoxychlorophosphine yields the phosphoramidite 9. All the stages were carried out with excellent yields. The derivative (9) was characterized by $^1$H and $^{31}$P NMR.

SCHEME 2
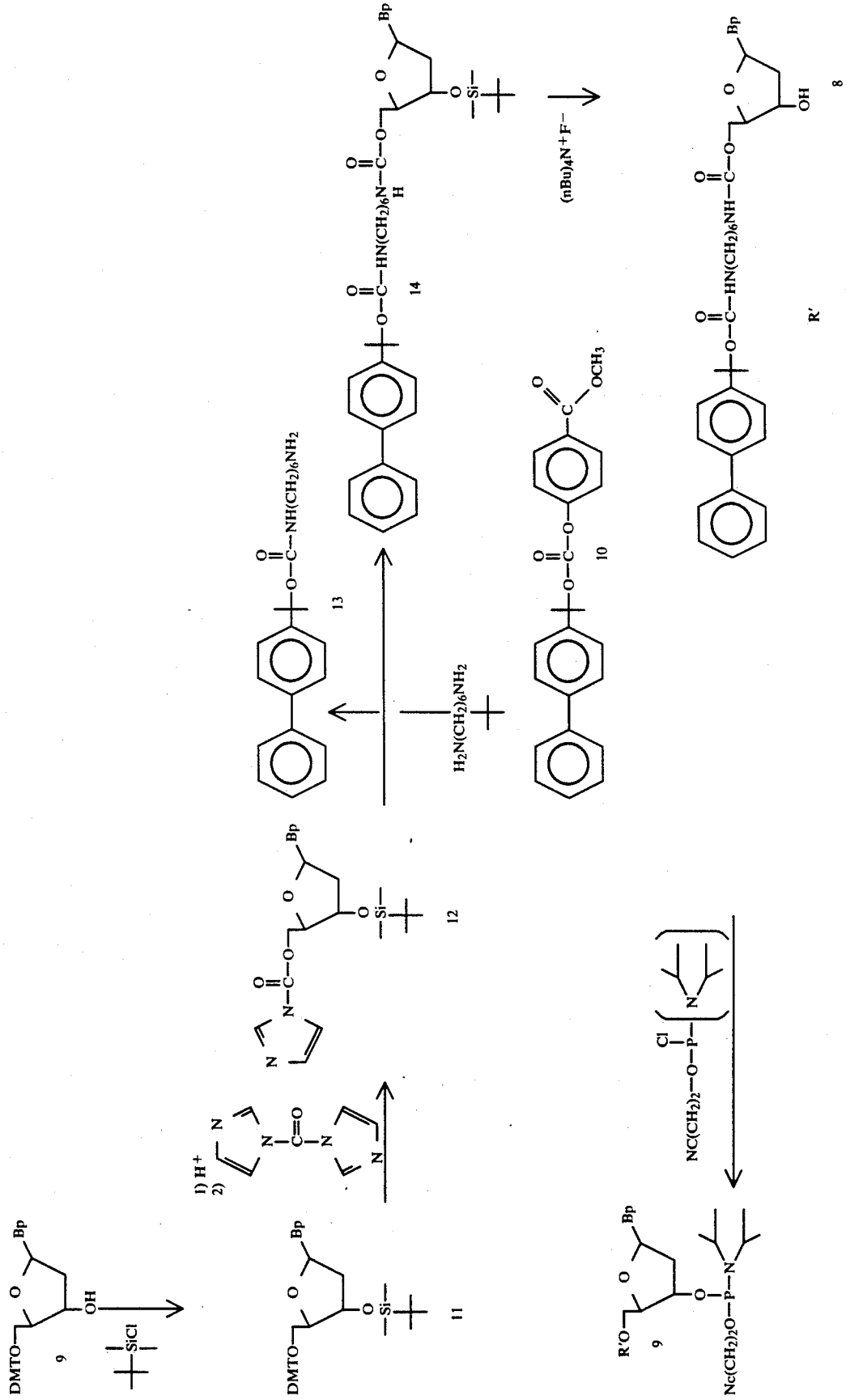

The starting derivative for the synthesis, thymidine, was converted to 3'-O-tert-butyldimethylsilylthymidine 11 in essentially three stages, as described below.

Synthesis of 3'-O-tert-butyldimethylsilylthymidine from thymidine

1st Stage

Thymidine (1.25 g; $5 \times 10^{-3}$ mole) is dissolved in anhydrous pyridine (25 ml). 4,4'-Dimethoxytrityl chloride (1.99 g; $6 \times 10^{-3}$ mole) is added and the reaction mixture is then stirred for 2 h at 20° C. Methanol (10 ml) is added and, after 10 minutes' stirring, the solution is diluted with 50 ml of of dichloromethane and washed with $3 \times 50$ ml of 5% strength NaHCO$_3$ solution in water. The solution is dried over Na$_2$SO$_4$ and filtered, and the solvents are evaporated off. The residue is purified on a Merck 9835 silica (60 g) column, eluting first with dichloromethane (300 ml)/pyridine (0.01%), then with dichloromethane (150 ml)/MeOH (1%)/pyridine (0.01%), and finally with 450 ml of dichloromethane/MeOH (2%)/pyridine (0.01 %). The fractions containing 5'-O-(4,4'-dimethoxytrityl)thymidine are concentrated. The residue is taken up in dichloromethane (40 ml) and precipitated, dropwise and with stirring, in hexane (350 ml). The white precipitate is dried under vacuum. Weight obtained 2.18 g; Yield=90%.

2nd Stage

5'-O-(4,4'-Dimethoxytrityl)thymidine (4.35 g; $8 \times 10^{-3}$ mole) and imidazole (2.25 g; $3.35 \times 10^{-2}$ mole) are introduced into a two-necked round-bottomed flask under argon, and treated with a solution of dimethyl-tert-butylchlorosilane (2.4 g; $1.6 \times 10^{-2}$ mole) in dimethylformamide (40 ml). The reaction mixture is stirred for 5 h at 20° C. and then poured into a water/ice mixture (450 ml). The precipitate is filtered off and taken up in dichloromethane (100 ml). The organic phase is washed once with 5% strength aqueous NaHCO$_3$ solution (100 ml), dried over MgSO$_4$ and concentrated. The residue is dried under vacuum. Weight obtained 5.13 g; Yield=97%.

3rd Stage

A 3% strength trichloroacetic acid solution in dichloromethane (300 ml) is added to 15 g ($2.28 \times 10^{-2}$ mole) of 5'-O-(4,4'-dimethoxytrityl)-3'-O-dimethyl-tert-butylsilylthymidine. The reaction mixture is stirred for ½ h at 20° C., then washed to neutrality with 5% strength aqueous NaHCO$_3$ solution, dried over Na$_2$SO$_4$, filtered and concentrated by evaporation of the solvents. The residue is purified on a Merck 9835 silica (350 g) column, eluting first with pure dichloromethane, then with dichloromethane/ethyl acetate (70:30 V/V) and finally with ethyl acetate/dichloromethane (50:50 V/V). The fractions containing the product are evaporated. The white solid residue is dried under vacuum. Weight obtained 8.7 g; Yield=89%. The product was monitored by TLC on silica and characterized by $^1$H NMR.

Process for preparing 2-(4-biphenylyl)propyl-2-oxycarbonylamido-6-hexylamine 13

1,6-Diaminohexane (2.034 g; $1.75 \times 10^{-2}$ mole) and 2-(4-biphenylyl)prop-2-yl 4-methoxycarbonylphenyl carbonate (10) (1.71 g; $4.38 \times 10^{-3}$ mole) are dissolved in dioxane (60 ml). The reaction mixture is stirred at 21° C. for 26 h. 5% strength Na$_2$CO$_3$ in water is added to the mixture. The aqueous phase is extracted with 100 ml of dichloromethane. The organic phase is washed once with 5% strength Na$_2$CO$_3$ in water and twice with water, and then dried over sodium sulfate and filtered. The solvents are evaporated off. The residue is purified by chromatography on a Merck 9835 silica column, eluting first with dichloromethane (600 ml), then with dichloromethane/methanol (98:2) (200 ml) and finally with dichloromethane/methanol/Et$_3$N (93:5:2) (100 ml). The fractions containing the product are evaporated and the residue is dried under vacuum. Weight obtained: 1.08 g; Yield=90%. The product was monitored by TLC on silica and characterized by $^1$H NMR.

This type of derivative is extremely useful, since it possesses two completely equivalent nucleophilic groups, one of which is selectively and temporarily protected. The free amino group can react to form a covalent link with a molecule possessing an electrophilic center. Subsequently, the protective group on the second amino group can be removed under very mild acid conditions, regenerating a further nucleophilic center.

Process for preparing 5'-[2-(4-biphenylyl)propyl-2-oxycarbonylamido-6-hexylamidocarboxy]-3'-O-tert-butyldimethylsilylthyidine 14

A solution of carbonyldiimidazole (0.534 mg; $3.3 \times 10^{-3}$ mole) in dioxane (4.8 ml) is added to a solution of 3'-O-tert-butyldimethylsilylthymidine (1.068 g; $3 \times 10^{-3}$ mole) in dioxane (12 ml), placed in a two-necked flask under argon. The reaction mixture is stirred for 5 h at 50° C., and then treated with a solution of 2-(4-biphenylyl)propyl-2-oxycarbonylamido-6-hexylamine 13 (1.41 g; $4 \times 10^{-3}$ mole) in dimethylformamide (7.2 ml). The reaction mixture is stirred from 20 h at 20° C. and then hydrolyzed with 5% strength aqueous NaHCO$_3$ solution (100 ml). The aqueous phase is extracted with dichloromethane (100 ml) and the organic phase is washed twice with 5% strength aqueous NaHCO$_3$ solution, filtered and dried over Na$_2$SO$_4$. The solvents are evaporated off and the residue is purified on a Merck 9835 silica column, eluting with dichloromethane. The fractions containing the product are evaporated. Weight obtained: 2.06 g; Yield=93%. The product was monitored by TLC on silica and characterized by $^1$H NMR.

Process for preparing 5'-[2-(4-biphenylyl)propyl-2-oxycarbonylamido-6-hexylamidocarboxy]thymidine 8

Tetrabutylammonium fluoride (3.6 g; $11.2 \times 10^{-3}$ mole) is added to a solution of 5'-[2-(4-biphenylyl)propyl-2-oxycarbonylamido-6-hexylamidocarboxy]-3'-O-tertbutyldimethylsilylthymidine 14 (2.06 g; $2.8 \times 10^{-3}$ mole) in tetrahydrofuran. The reaction mixture is stirred for ½ h at 20° C. and the solvents are then evaporated off. The residue is purified by chromatography on a Merck 9835 silica column, eluting first with dichloromethane and then with CH$_2$Cl$_2$/MeOH (95:5 V/V). The fractions containing the product are evaporated. Weight obtained 3.99 g; Yield=93%. This product was monitored by TLC on silica and characterized by $^1$H NMR.

Process for preparing
5′-[2-(4-biphenyl)propyl-2-oxycarbonylamido-6-hexylamidocarboxy]-3′-O-[N,N-diisopropylamino)cyanoethoxyphosphino]thymidine 9

Diisopropylamine (0.68 ml) and cyanoethoxydiisopropylaminochlorophosphine (0.39 ml; $1.9 \times 10^{-3}$ mole) are added successively to a solution of 5′-[2-(4-biphenylyl)propyl-2-oxycarbonylamido-6-hexylamidocarboxy]thymidine 8 (0.622 g; $10^{-3}$ mole) in anhydrous tetrahydrofuran (8μ), stirred under argon in a two-necked flask. The reaction mixture is stirred for ½ h at 20° C. and filtered. Ethyl acetate 10 ml) is added to the filtrate, and the solution obtained is washed three times with 10 ml of 5% strength aqueous NaHCO$_3$ solution, dried over Na$_2$SO$_4$, filtered and then concentrated to dryness. The residue is purified by chromatography on a Merck 9835 silica column, eluting with ethyl acetate/hexane (70:30 V/V). The fractions containing the product are evaporated, and the residue is dissolved in 4 ml of dichloromethane and then precipitated in 50 ml of hexane at −90° C. with stirring and under argon. The white solid is filtered off and dried under vacuum. Weight obtained: 0.68 g; Yield=82%. The product was monitored by TLC on silica and characterized by $^1$H and $^{31}$P NMR.

EXAMPLE II

Study of the Reactivity of the Derivative 9

This type of nucleotide derivative can be used for linking synthetic DNA molecules covalently to natural macromolecules such as enzymes, to synthetic polymers or to fluorescent molecules or molecules capable of forming very stable complexes with macromolecules such as, for example biotin. It finds applications in biological and biomedical research, and especially in the diagnostic field. This derivative can be introduced in a single stage at the end of an oligodeoxyribonucleotide, under standardized conditions of automatic solid phase synthesis, yielding in one elongation cycle a reactive chemical group remote from the oligonucleotide skeleton.

The phosphoramidite 9 was reacted in solution in acetonitrile with 3′-O-levulinylthymidine in the presence of tetrazole, and the kinetics of the coupling reaction were followed in parallel with the known kinetics for the derivative 3′-O-[(N,N-diisopropylamino)cyanoethoxyphosphino]-5′-O-(dimethoxytrityl)thymidine, by thin layer chromatography (TLC) and by $^{31}$P NMR.

The results show that the rate of formation of the internucleotide link is comparable with both derivatives. Solid phase coupling of the derivatives of general formula 9 is carried out under conditions identical or similar to those for the derivatives customarily used in oligonucleotide synthesis.

The lability of the protective group on the terminal amine was also studied in solution, in parallel with that of the DMT derivative of thymidine. Under the conditions customarily employed (3% strength trichloroacetic acid in CH$_2$Cl$_2$), the rates of deprotection of both groups are comparable. These results were confirmed in the solid phase.

The derivative 9 (where Bp=T) was condensed in the automatic oligonucleotide synthesis apparatus with thymidine bound to the solid support, and the protective group on the amine was removed automatically. All the conditions (times, concentrations and solvents) customarily used during an oligonucleotide elongation cycle were reproduced on an ABS 380A synthesizer. After cleavage from the solid support with ammonia solution, the crude product was analyzed by HPLC, and the result compared with that obtained after condensation performed in parallel with the derivative 3′-O-[(N,N-diisopropylamino)cyanoethoxyphosphino]-5′-O-(dimethoxytrityl)thymidine.

In each case, a virtually pure product is obtained. The two dimers are distinguished clearly by their retention times in HPLC. These results show that the solid phase condensation, oxidation and deprotection reactions are effective, and do not degrade the new dimer. In addition a study performed on the stability of the new carbamate bond confirms that it is resistant to ammoniacal treatment under the conditions for deprotection of the bases.

Solid Phase Coupling of the Derivative 9 with an (Oligo)Nucleotide Bound to an Insoluble Support The derivative 9, solubilized in acetonitrile at a concentration of 0.1M, is activated with 0.5M tetrazole in the same solvent, and condensed with the hydroxyl group at the 5′ position of thymidine bound to an insoluble polymer customarily used in oligodeoxyribonucleotide synthesis on an ABS 380A synthesizer. All the conditions are identical to those used in an oligonucleotide elongation cycle (N. D. Sinha, J. Biernat, J. McManus & H. Köster Nucleic Acids Research 12 (11) 4539 (1984)), including the acid deprotection of the terminal amino group. The cleavage of the product from the solid support is carried out under the customary conditions, and the final product is obtained in a yield comparable to those commonly achieved in oligonucleotide synthesis.

EXAMPLE III

Preparation of Mixed Oligodeoxyribonucleotide/Synthetic or Natural Macromolecule Molecules Which are Useful in the Detection of DNA Sequences by Non-radioactive Methods The synthesis and use of mixed molecules, composed of an oligodeoxynucleotide portion and another portion possessing properties, enable deoxyribonucleic acid targets to be detected easily and rapidly by non-radioactive methods. The oligodeoxyribonucleotide portion having a defined sequence homologous with a target DNA fragment contributes the energy of stabilization which provides for its hybridization with the DNA molecule which it is desired to detect. The portion which supplies the radioactivity enabling the hybrid to be detected is coupled through a covalent chemical link with the oligodeoxyribonucleotide. Among the different molecules possessing the properties required for the detection, polybiotinylpolyethylenimine, polyfluoresceinylpolyethylenimine, microperoxidase and alkaline phosphatase are preferably used.

The process for preparing such mixed compounds, shown in Scheme 3 below, comprises either four stages or three main stages, depending on the nature of the detectable portion of the molecule, designated the "labeling component" M.

1) Solid phase synthesis of the oligodeoxyribonucleotide by one of the various known methods.

2) Extension at the 5′ position of the oligonucleotide in the solid phase by a chemically modified nucleotide bearing a chain (designated "arm") having at its end a functional group ($R_1$) which, after activation with a bifunctional reagent, establishes the covalent link with the molecule "M".

3) Grafting, where appropriate, of detectable molecular groups onto a polymer in order to prepare M.

4) Coupling the modified oligodeoxyribonucleotide with the molecule "M".

The coupling reaction 4) is accomplished with the oligonucleotide molecule, either still bound to the solid synthesis support, or after cleavage when the stability of the molecule "M" is incompatible with the cleavage conditions.

The oligonucleotide synthesis can be carried out by the phosphite or the phosphate method, manually or in an automatic synthesis apparatus as described in the specialist scientific literature of the field.

The introduction of the chemical arm needed for coupling with the molecule "M" is carried out via a nucleotide modified according to Example I, which can be, in particular, thymidine, deoxyadenosine, deoxycytidine, deoxyguanosine or deoxyinosine, chemically protected on the base, to which the "arm" has been bound at its 5' end by a series of controlled chemical reactions carried out in solution. These reactions comprise the selective protection of the hydroxyl group at the 3' position, the activation of the hydroxyl group at the 5' position and reaction with a singly protected dinucleophile which creates a stable carbamate link. The dinucleophile is a singly protected diamine, newly prepared for the requirements of the synthesis.

The hydroxyl group at the 3' position of the nucleoside is liberated from its protective group and phosphorylated with reagents which permit the solid phase coupling of the modified nucleotide, either by the phosphate triester method, or by the phosphite method, with a chemically protected oligodeoxyribonucleotide.

cyanate group in the case of fluorescein isothiocyanate. Under non-saturating conditions, nucleophilic groups remain for coupling the labeled polymer to the oligonucleotide bearing the nucleophilic "arm". This coupling is hence carried out via a bifunctional reagent such as a diepoxide, diisocyanatohexane or suberic acid N-hydroxysuccinimide diester.

1) Biotinylation of polyethylenimine PG35

The binding of biotin to polyethylenimine was studied taking tritiated N-hydroxysuccinimidobiotin as a model. After the reactants have been stirred for several hours in a medium containing 0.1M $NaHCO_3$, separation between the polymer molecules and the free biotin molecules is performed in two stages: dialysis in a phosphate buffer followed by molecular filtration. The degree of incorporation is measured by radioactivity. The conditions developed on this model can be reproduced with a more sophisticated reagent such as biotinamidocaproate N-hydroxysuccinimide ester, which enables the steric hindrance between the biotinyl rings and the polymer skeleton to be relieved, facilitating the approach of the avidin complexes to be used for the amplification and detection.

These biotinyl groups exhibit a very high affinity for avidin (or streptavidin) and for its conjugated analogs (conjugated to peroxidase or to alkaline phosphatase). The conjugated biotin-avidin complexes can then be detected by the action of the conjugated enzyme on a chromogenic substrate such as 5-bromo-4-chloro-3-indolyl phosphate and nitrotetrazolium blue.

Polyethylenimine was biotinylated by stirring for 24 hours 700 μl of a 10% strength solution of PG35 (BASF) (50 μmol) with 198 mg (580 μmol) of N-hydroxysuccinimidobiotin in which a fraction of the molecules is tritiated at the 8–9 position (Amersham).

SCHEME 3

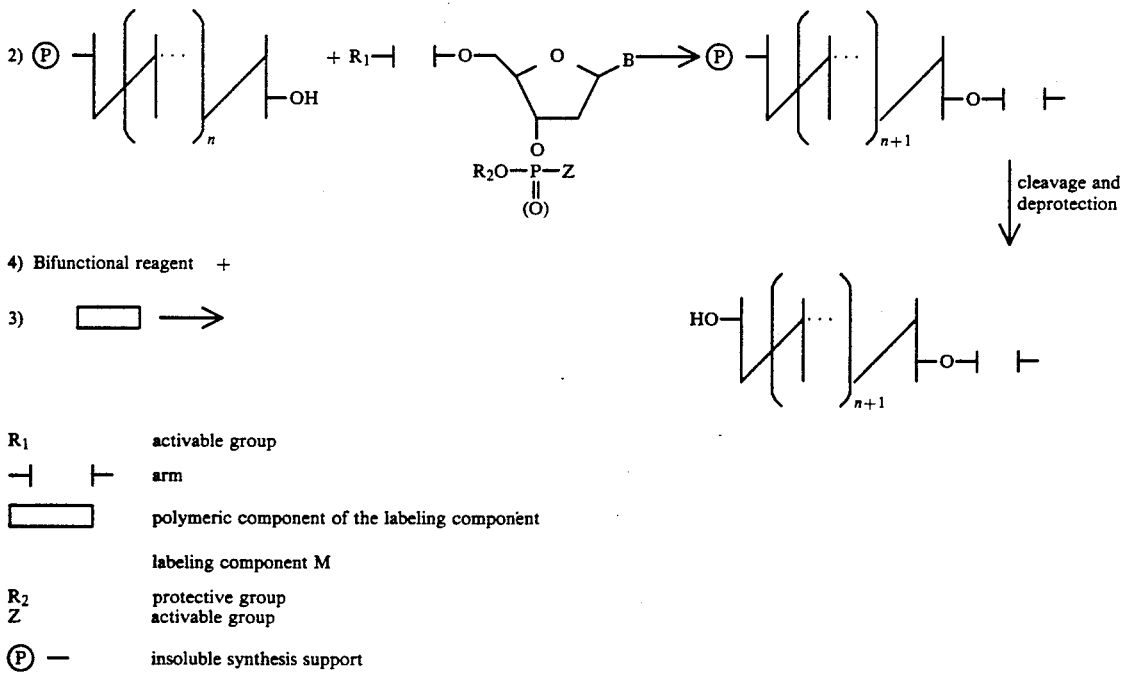

| | |
|---|---|
| $R_1$ | activable group |
| ⊣ ⊢ | arm |
| ▭ | polymeric component of the labeling component |
| | labeling component M |
| $R_2$ | protective group |
| Z | activable group |
| ⓟ — | insoluble synthesis support |

The labeling of the chemical polymers is carried out via the nucleophilic groups, by reaction either with activated esters in the case of biotin, or with the isothio- The reaction mixture is then dialyzed against 5 mM Na$_2$PO$_4$ solution (pH 8.2). It is dialyzed for 3 times 0.5 hours against 40 cc of phosphate buffer. The contents of the dialysis sack is then lyophilized and the residue is purified by chromatography on a Sephadex G-25 column, eluting with H$_2$O.

The degree of incorporation, measured by radioactivity, indicates an incorporation of 9.3 molecules of biotin per molecule of polymer (M$\overline{w}$ 1400).

2) Process for Preparing an Oligodeoxyribonucleotide Probe Coupled to Biotinylated Polyethylenimine A DNA probe was synthesized with an oligodeoxynucleotide sequence homologous with a specific region of the DNA of a human papilloma virus (HPV) type comprising 24 nucleotides.

In the solid phase in an automatic apparatus, a probe of sequence 5' TGG GCT CTG TCC GGT TCT GCT TGT 3' is prepared in which the 24th nucleotide T is modified as described in Example 1. To this end, 6 mg of CPG support functionalized with dimethoxytritylthymidine to the extent of 34 μmol/g, corresponding to 0.2 μmol, were used. After automatic assembly of the icosatetramer (24-mer), the functionalization of the oligodeoxyribonucleotide chain with the biotinylated polymer was carried out in three different ways:

A. functionalization on a solid support with the biotinylated polymer;
B. functionalization on a solid support with the non-biotinylated polymer, followed by biotinylation of the bound polymer;
C. binding of the biotinylated polymer in solution, after cleavage of the chain from the support.

Method A: Functionalization on a Solid Support with the Biotinylated Polymer

The 24-mer in which the 24th nucleotide T has been modified (alkylamino chain) is prepared in the synthesizer as described above. The amine terminating the chain is automatically deprotected by treatment with trichloroacetic acid, and the column containing the oligomer bound to silica is then removed from the apparatus and treated in the following manner: the column is washed, using a syringe, with 2 cc of dry acetonitrile and then dried with argon and treated for 2 h 30 min with 250 μl of a 0.1M solution of suberic acid bis(N-hydroxysuccinimide ester) in dry DMF. The column is then washed, using the syringe, with 2 cc of dry DMF followed by 2 cc of dry acetonitrile, and dried with argon. The column is then treated for 14 hours with 250 μl of a 0.032M solution of PG35.4 biotin in a 50:50 0.1M NaHCO$_3$/DMF mixture. The column is then washed, using the syringe, with 4 cc of water followed by 2 cc of acetonitrile and dried with argon. The deoxyribonucleotide chain thus functionalized is cleaved from the CPG support by 4 successive 0.5-hour treatments with 500 μl of 25% strength NH$_4$OH. The combined ammoniacal solutions are lyophilized, the residue is dissolved in 3 cc of 25% strength NH$_4$OH and the solution is maintained for 5 hours at 50° C. The object of this second ammoniacal treatment is to deprotect the bases and phosphates of the oligonucleotide chains. The solution is then lyophilized, and the residue is subjected to chromatography by molecular filtration (Sephadex G-50 gel) followed by polyacrylamide gel electrophoresis.

Alternatively, the final purification is performed by HPLC on an exclusion chromatography column (pH 7.9 phosphate buffer, isocratic elution).

Method B: Functionalization on a Solid Support with the Non-biotinylated Polymer, Followed by Biotinylation of the Bound Polymer The 24-mer in which the 24th nucleotide T has been modified (alkylamino chain) is prepared in the synthesizer as described above. The amine terminating the chain is automatically deprotected by treatment with trichloroacetic acid, and the column containing the oligomer bound to silica is then removed from the apparatus and treated in the following manner: the column is washed, using a syringe, with 2 cc of dry acetonitrile and then dried with argon and treated for 2 h 30 min with 250 μl of a 0.1M solution of suberic acid bis(N-hydroxysuccinimide ester) in dry DMF. The column is then washed with 2 cc of dry DMF and then 2 cc of dry acetonitrile, and dried with argon. It is then treated for 19 hours with 10 μmol of polyethylenimine PG35 (140 μl of a 10% strength solution diluted with 160 μl of a 50:50 0.1M NaHCO$_3$/DMF solution). The column is then washed with 4 cc of saturated aqueous sodium citrate solution followed by 4 cc of water and 2 cc of acetonitrile, and dried with argon. The column is then treated for 15 hours with 250 μl of a 0.05M solution of tritiated N-hydroxysuccinimidobiotin. The column is then washed with 4 cc of water and 2 cc of acetonitrile, and dried with argon. The oligodeoxyribonucleotide chain thus functionalized is cleaved from the support by 4 successive ½-hour treatments with 500 μl of 25% strength NH$_4$OH. The ammoniacal solutions are combined and lyophilized, and the residue is then dissolved in 3 cc of 25% strength NH$_4$OH; the solution obtained is maintained for 5 hours at 50° C. The object of this second ammoniacal treatment is to deprotect the bases and phosphates of the oligonucleotide chains. The solution is then lyophilized; the residue is subjected to molecular filtration chromatography (Sephadex G-50 gel), followed by polyacrylamide gel electrophoresis.

Alternatively, the final purification is performed by HPLC on an exclusion chromatography column (pH 7.9 phosphate buffer, isocratic elution).

Method C: Binding of the Biotinylated Polymer in Solution after Cleavage of the Chain from the Support The 24-mer in which 24th nucleotide T has been modified is prepared in the synthesizer as described above. Deprotection with trichloroacetic acid of the amine terminating the oligonucleotide chain and cleavage of the chain from the support with 25% strength ammonia solution are performed automatically in the apparatus. The ammoniacal solution obtained, containing the nucleotide chain, is brought to 3 cc with 25% strength NH$_4$OH solution; it is treated for 5 hours at 50° C. and then lyophilized. The residue is subjected to molecular filtration chromatography (Sephadex G-50 gel), followed by polyacrylamide gel electrophoresis. The oligodeoxyribonucleotide thus synthesized and purified is subjected to a series of treatments in solution for the purpose of binding the biotinylated PG35 polymer: 1.2 O.D. of oligomer are dissolved in 12 μl of an aqueous solution which is 0.1M with respect to NaHCO$_3$ and 2 mM with respect to EDTA. 25 μl of a solution of suberic acid bis(N-hydroxysuccinimide ester) in dry DMSO (10 mg/ml) are added. The reaction mixture is left for 10 minutes at room temperature and then purified on a Sephadex G-25 column, eluting with H$_2$O. The first fraction containing the oligomer is cooled as it emerges from the column and lyophilized. After lyophilization, 80 nmol of PG35.4 biotin, dissolved in 100 μl of an aqueous solution containing 0.1M NaHCO₃ and 3M NaCl are added to the residue. The reaction mixture is maintained for 20 hours at room temperature, and then subjected to molecular filtration chromatography.

For the coupling, the oligonucleotide containing the aminated chemical arm at its 5' end can be activated with, as a bifunctional reagent, apart from suberic acid bis(N-hydroxysuccinimide ester), 1,2,7,8-diepoxyoctane or 1,6-diisocyanatohexane.

EXAMPLE IV

Use of the Oligodeoxyribonucleotide Probe Linked to Biotinylated Polyethylenimine in the Detection of Human Papilloma Viruses The value of the biotin-labeled mixed oligodeoxyribonucleotide/macromolecule molecule described above was exemplified in hybridization and detection experiments in which the target DNA molecule is the genome of human papilloma virus 16. The mixed molecule prepared according to one of the methods described above hybridizes specifically with HPV16 DNA to the exclusion of DNA sequences of other HPV viruses. The detection of the hybrid molecules was accomplished by means of conjugated biotin-streptavidin complexes, by the action of the conjugated enzyme peroxidase or alkaline phosphatase on the chromogenic substrates diaminobenzidine or 5-bromo-4-chloro-3-indolyl phosphate and nitrotetrazolium blue, respectively.

The DNA of HPV16 and HPV18, cloned into plasmid vectors, was deposited in parallel on nylon filters or on nitrocellulose filters. These filters were prehybridized in 5× SSPE 5× Denhart, 0.5% SDS, 0.2 μ/ml salmon sperm DNA, either at 45° C. or at 60° C. The filters were hybridized in this hybridization mixture containing 0.1 μg/ml of salmon sperm DNA and 200 ng of biotinylated HPV16 probe, either at 45° C. or at 60° C. The filters were washed in 2× SSPE, 0.1% SDS at room temperature for 2×10' and 10' in 5× SSPE, 0.1% SDS at 60° C. or 45° C. Several different processes were used subsequently.

Process 1

The non-specific sites were blocked for 1 h at 37° C. in buffer A (0.1M Tris-HCl pH 7.5, 1M NaCl, 2 mM MgCl₂, 0.5% Tween 20 ™, 0.05% TRITRON X100 ™ wetting agent) containing 3% of BSA. The filters were washed 2× in this buffer A, and then incubated in buffer B (0.1M Tris, 1M NaCl, 2 mM MgCl₂, 0.05% Triton X100 and 0 05% Tween 20 ™ surfactant) in the presence of a biotinylated peroxidase-streptavidin complex for 1 h at room temperature. The filters were then washed 5× in buffer A containing 1% BSA, then 2× in buffer C (20 mM Tris-Hcl pH 7.5, 0.5M NaCl) and incubated for at least 30' in buffer C in the presence of diaminobenzidine and H₂O₂.

Process 2

The filters were blocked for 20 minutes at 42° C. in buffer 1 (0.1M Tris-HCl pH 7.5, 0.1M NaCl, 2 mM MgCl₂, 0.05% Triton X-100 containing 3% BSA). The filters were then dried for 20 minutes at 80° C. under vacuum, and rehydrated in buffer 1 in the presence of BSA. The filters were then incubated for 10 minutes in buffer 1 containing 1 μ/ml of biotinylated calf alkaline phosphatase. After being washed in buffer 1, and then in buffer 3 (0.1M Tris-HCl pH 9.5, 0.1M NaCl, 50 nM MgCl₂), the filters were incubated for not more than 4 hours protected from the light in buffer 3 containing nitrotetrazolium blue and 5-bromo-4-chloro-3-indolyl phosphate.

1 Femtomole of HPV16 DNA can be specifically and readily detected by both methods with both types of filters, although the nylon filters show a high background. The HPV18 DNA used in parallel as a negative control does not stain at all.

FIG. 1 shows the visualization of the hybridization of HPV16 DNA with a polybiotinylated DNA probe as described above for HPV16.

The DNA was deposited on nitrocellulose filters.
Row 1 contained HPV16 DNA cloned into pBR322.
Row 2 contained HPV18 DNA cloned into pBR322.
The different filters corresponded, for
A to 5 μg of DNA
B to 1 μg of DNA
C to 0.1 μg of DNA
D to 10 ng of DNA
E to 1 ng of DNA
F to 0.1 ng of DNA.

The hybridization was carried out according to process 2 in the prehybridization mixture in the presence of 200 ng of biotinylated HPV16 probe per ml of medium. A visualization of the hybridization is observed for 10 ng of HPV16 DNA.

EXAMPLE V

Probe Directly Labeled with Biotin with Detection after Amplification of the DNA to be Detected 1) Automatic Synthesis of a 29-mer Oligonucleotide Specific for HPV16 and Containing 5'-(Alkylamino)Thymidine at the End of the Chain The 29-mer oligonucleotide specific for HPV16 synthesized is as follows:

5' TAC GCA CAA CCG AAG CGT AGA GTC
    ACA CT 3' alkylamino

It was prepared by the phosphoramidite method (McBride L. J. and Caruthers, M. H., Tetrahedron Lett. 24 (1983) 245–248) on an Applied Biosystems 380A synthesizer. The synthesis was conducted on the 0.2 μmol scale, using 2-cyanoethyl-N,N-diisopropylphosphoramidites.

The last phosphoramidite introduced onto the oligonucleotide chain is the synthon whose synthesis has been described above:

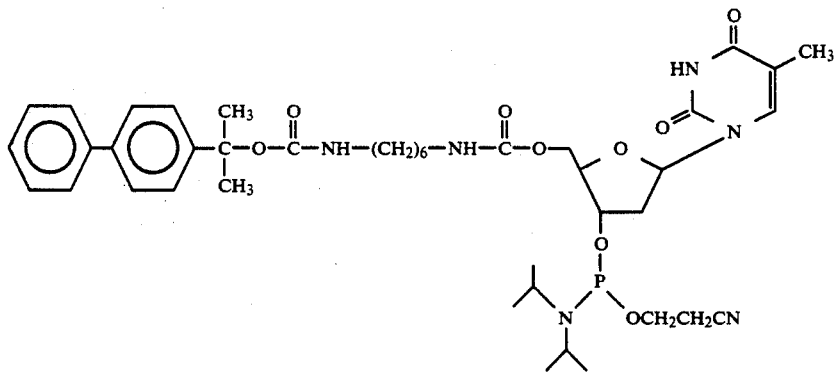

After (automatic) removal of the protective group (diphenylisopropyloxycarbonyl) at the end of the oligonucleotide chain with 3% strength trichloroacetic acid in dichloromethane, the "controlled porous glass" (CPG) support bearing the 5′-alkylamino oligonucleotide chain is treated as described above for the purpose of labeling with biotin.

2) Labeling of a 5′-alkylamino oligonucleotide specific for HPV16 with sulfosuccinimidyl 6-(biotinamido)hexanoate The use of this biotin derivative has the effect of lengthening the distance from the oligonucleotide. The new link thus created between the biotin and the oligonucleotide is a $C_{12}$ hydrocarbon group. The sulfosuccinimidyl group is a leaving group substituted with the terminal amine of the $C_6$ arm linked to the oligonucleotide.

a) In the Solid Phase

One half of the CPG support bearing the 5′-alkylamino oligonucleotide chain (0.1 μmol) (see preparation above) is treated for 16 hours with 250 μl of a 0.1M solution of sulfosuccinimidyl 6-(biotinamido)hexanoate (Pierce 21335) in dry dimethylformamide (the dimethylformamide has been treated overnight with barium oxide and then filtered and distilled over potassium hydroxide, pressure: 15 mm Hg).

The support is then washed with water (4×2 cc) and thereafter treated with a 25% strength ammoniacal solution (4×250 μl; ¼ h) in order to effect the cleavage of the oligonucleotide chain from the support. The combined ammoniacal solutions are heated for 5 hours to 55° C. in order to deprotect the primary amines of the bases of the oligonucleotide chain, and then lyophilized. The residue obtained is desalted on a SEP-PAK C18 column (1st elution, 5 cc water; 2nd elution 5 cc 20% CH₃CN/80% water). 9.3 $OD_{257}$ of crude product are obtained (sample 1 tested in hybridization, see below).

Six $OD_{257}$ of the crude product (sample 1) were purified by electrophoresis (20% polyacrylamide gel, 1.5 mm). The biotinylated product is then removed from the gel by electroelution (15 mM Tris-HCl pH 8.3); the solution obtained is lyophilized and constitutes sample 2 (0.375 $OD_{255}$), tested in hybridization below.

Apart from the biotinylated product, a further 1.02 $OD_{257}$ of starting 5′ alkylamino oligomer, which constitutes sample 3 tested in hybridization below, is recovered.

b) In the Liquid Phase

One half of the CPG support bearing the 5′ alkylamino oligonucleotide chain (0.1 μmol) (see preparation above) is treated with 25% strength ammonia solution 4×250 μl; ¼ h) in order to cleave the oligonucleotide chain support. The combined ammoniacal solutions are heated for 5 hours to 55° C., in order to deprotect the primary amines of the bases of the oligonucleotide chain, and then lyophilized. The residue obtained is eluted on a Sephadex G-50 column (10 ml) (eluent: 10 mM TEAB), and then purified on polyacrylamide gel (20%, thickness 1.5 mm). The oligonucleotide is recovered by electroelution (15 mM Tris-HCl pH 8.3). The oligonucleotide solution obtained (5.4 $OD_{257}$) is lyophilized.

Two $OD_{257}$ of 5′-alkylamino oligonucleotide are dissolved in 20 μl of 0.2M HEPES buffer (pH 7.6). 100 μl of a 0.1M solution of sulfosuccinimidyl 6-(biotinamido)-hexanoate in dimethylformamide are added to the solution. The reaction mixture is left for 16 hours at room temperature and then eluted on a Sephadex G-50 column (10 ml; eluent: 100 mM TEAB). 1.96 $OD_{257}$ of crude product are harvested, for which the hybridization tests gave, from the standpoint of both selectivity and sensitivity, the same results as sample 1 (crude product of solid phase biotinylation).

3) Detection of Papilloma Virus 16 DNA Using the Biotinylated Oligomer a) Isolation of Cells from Uterine Cervical Biopsies The tumor biopsies are initially cut up with a scalpel into approximately 3 mm³ pieces. These pieces are then suspended in a PBS saline buffer (1X:15 mM NaCl, 2 mM KH₂PO₄) and thereafter digested with 0.25% trypsin in PBS. The disaggregated cells are then counted.

b) Enzymatic Amplification in Vitro of Papilloma Virus (HPV) DNA

The DNA of different tumors was employed in enzymatic amplification reactions according to a process similar to that described by Saiki (Ref. 1). Three pairs of specific primers, each of an HPV type, were used in this experiment (Ref. 2).

|  | Position in the HPV genome |
|---|---|
| Primers specific for HPV16 | |
| GCA GAA CCG GAC AGA GCC CA | 694–713 |
| GTG TGC CCA TTA AA GGT CTT CC | 820–798 |

|                                          | Position in the HPV genome |
|------------------------------------------|----------------------------|
| These primers define a 127-bp fragment.  |                            |
| Primers specific for HPV18               |                            |
| GCCCGACGAGCCGAACCACA                     | 740–759                    |
| GGAATGCTCGAAGGTCGTCTG                    | 848–828                    |
| These primers define a 109-bp fragment.  |                            |
| Primers specific for HPV33               |                            |
| GGCTTGGACCGGCCAGATGG                     | 681–700                    |
| GTGCACAGGTAGGGCACACAA                    | 858–839                    |
| These primers define a 178-bp fragment.  |                            |

The amplification reaction is carried out in a volume of 50 µl of mixture containing six thousand tumor cells, 16.6 mM $(NH_4)_2SO_4$, 67 mM Tris-HCl pH 8.8, 6.7 mM $MgCl_2$, 10 mM ME, 200 µm dATP, dCTP, dGTP, dTTP, 200 µg/ml of gelatin and 30 picomoles of each of the primers, 0.25% DMSO, 1 unit of heat-stable polymerase (Taq polymerase, New England Biolabs). A drop of mineral oil is added and the mixture is incubated for 10 minutes at 92° C. It is then incubated successively for 1 minute at 92° C. and 3 minutes at 66° C., and the cycle is repeated thirty times.

c) Preparation of the Filters for Hybridization with Biotinylated Oligomer

On the one hand, the DNA cloned into pBR322, of HPV6b, 11, 16, 18 and 33 was denatured for 15, at 45° C. in 0.5N NaOH. Each clone was filtered on a nylon membrane in the presence of 0.1 µg of carrier DNA, salmon sperm DNA. The filters are placed for 10 minutes on a pad impregnated with 0.5M NaOH, 1.5M NaCl, and 10 minutes on a pad impregnated with 0.5M Tris HCl pH 7.5, 1.5M NaCl, and rinsed for 5 minutes in 2XSSC (1XSSC=0.15M NaCl, 15 mM trisodium citrate pH 7.2). The filters are then dried in the air, and the DNA is thereafter fixed by UV irradiation (312 nm for 1 minute).

On the other hand, one fifth of the product of each enzymatic amplification is analyzed by electrophoresis on 4% Nusieve agarose gel. The gel is then incubated for 30 minutes in a 0.5M NaOH, 1.5M NaCl solution (denaturation of the DNA), and is then neutralized by incubation for 30 minutes in Tris-HCl pH 7.5, 1.5M NaCl. The DNA is transferred onto a nylon membrane by Southern's technique (Ref. 3) and fixed by UV irradiation.

d) Hybridization of the Filters

The filters are prehybridized in the following mixture: 5XSSPE (1XSSPE=0 18M NaCl, 10 mM $NaH_2PO_4$, 1 mM EDTA pH 8), 5X Denhart (1X Denhart=0.02% Ficoll, 0.02% BSA, 0.02% polyvinylpyrrolidone) and 0.1 mg/ml of salmon sperm DNA denatured at 45° C. for at least two hours.

Sample 1, 2 or 3, diluted (1 µg/ml) in the prehybridization mixture, is added, and the hybridization is carried out at 45° C. for 16 hours.

The filters are then washed for twice 15 minutes in 3XSSC, 0.1% SDS at room temperature and 10 minutes in 6XSSC, 0.1% SDS at 45° C.

e) Detection of the Biotinylated Hybrids

The filters are incubated for 20 minutes in a blocking solution at 42° C. (0.1M Tris-HCl pH 7.5, 0.1M NaCl, 2 mM $MgCl_2$, 0.05% Triton X-100=buffer 1+3% BSA=buffer 2). The filters are then dried, thereafter rehydrated in buffer 2 and thereafter incubated for 10 minutes in the presence of streptavidin (2 µg/ml of buffer 1). The filters are rinsed three times in buffer 1, then incubated for 10 minutes in the presence of biotin coupled to alkaline phosphatase (1 µg/ml buffer 1). The filters are rinsed twice in buffer 1 and then twice in buffer 3 (0.1M Tris-HCl pH 9.5, 0.1M NaCl, 50 mM $MgCl_2$).

The filters are then incubated in buffer 3 in the presence of the substrate for alkaline phosphatase, 5-bromo-4-chloro-3-indolyl phosphate (BCIP) and nitrotetrazolium blue (NBT). The staining reaction is stopped by washing in 20 mM Tris-HCl pH 7.5, 5 mM EDTA solution.

f) Results

We initially tested the sensitivity of detection of sample 1 on decreasing amounts ($10^{-13}$ to $10^{-16}$ moles: 100, 10, 1 and 0.1 fentomoles) of HPV6b, HPVII, HPV16, HVP18 and HPV33 clone DNA.

We were able to note that sample 1 is exclusively specific for HPV16, and that the detection threshold was in the region of one fentomole ($10^{-15}$).

We then tested this sample 1 is exclusively amplified tumor DNA. After half an hour of visualization, we were easily able to detect bands specific to HPV16.

We then tested samples 2 and 3 on the cloned DNA. Sample 2 has a detection threshold lowered by a factor of at least 10 ($10^{-16}$ mole) and retains the specificity for HPV16. Hybridization with sample 3 gives no visible signal, as expected, since it is not biotinylated.

REFERENCES

1. Saiki, R. K. et al (1988) Science 239, 487–491.
2. Sondes d×acides nucléiques des virus nucléiques des virus de papillome humain (Nucleic acid probes for nucleic acids of human papilloma viruses). Herzog et al., French patent 2,618,782 (1989) based on French patent application 8710917.
3. Southern, E. M. (1977) J. Mol. Biol. 98, 503.

We claim:

1. A nucleotide or nucleic acid of the formula

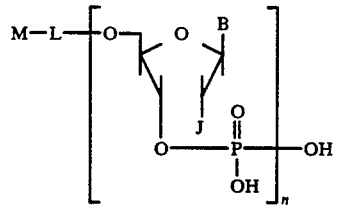

wherein:
J=H or OH;
n=1 to 100,000;
B=a purine or pyrimidine nucleic acid base;

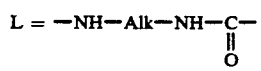

where Alk is a straight alkyl chain of from 2 to 20 carbon atoms; and
M=a non-radioactive detectable label.

2. A method of preparing a nucleic acid probe comprising:
(a) synthesizing a nucleic acid of formula Ia:

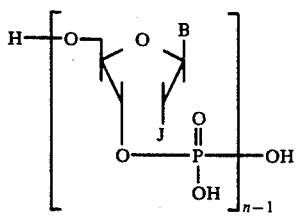

wherein:
J = H or OH;
n = an integer of up to 100,000 and n-1 is at least 1;
B = a purine or pyrimidine nucleic acid base;
(b) coupling said nucleic acid at its free 5'—(OH) end, to the 3'—(OH) of a nucleotide synthon which synthon is (1) protected at the 3' position by a phosphoryl group for linking to said 5' end of said sequence, (2) bonded at the 5' position to a linking group L terminating in a protective group $R_1$ capable of being activated for linking to a detectable label and (3) of the formula IV

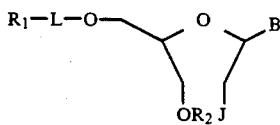

in which
J, B, and $R_1$ have the meanings given above, B optionally being protected,

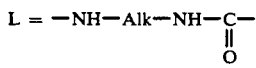

where Alk is a straight alkyl chain of from 2 to 20 carbon atoms,
$R_2$ is any phosphorylated group for joining to the 5' end of another nucleotide to give the compound of formula Ib

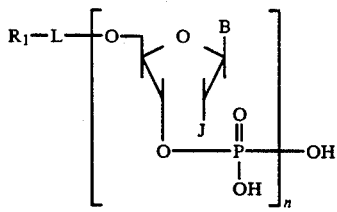

(c) activating $R_1$ and reacting activated $R_1$ with said detectable label to produce said probe.

3. A compound of the formula:

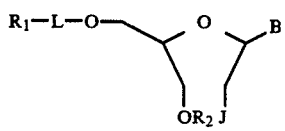

wherein:
J = H or OH;
B = a purine or pyrimidine nucleic acid base;

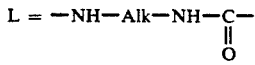

where Alk is a straight alkyl chain of from 2 to 20 carbon atoms;
$R_1$ = a protective group capable of being activated for linking to a detectable label; and
$R_2$ = H or a phosphorylated group for joining to the 5' end of a nucleotide, with the proviso that B may be substituted with protective groups.

4. A process for preparing a compound according to claim 3, said process comprising:
selectively activating the 5'OH of a 3'OH protected and base protected nucleotide;
coupling at the 5' position a singly protected linking group of the formula $R_1$—L—, wherein:

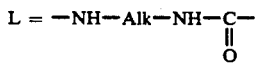

where Alk is a straight alkyl chain of from 2 to 20 carbon atoms and $R_1$ is a protective group capable of being activated for linking to a detectable label;
deprotecting said 3'—OH position; and
optionally, phosphorylating said 3'—OH with a phosphoryl group capable of coupling to the 5'—OH of a nucleoside or nucleotide.

5. A nucleotide or nucleic acid according to claim 1 wherein Alk is hexamethylene.

6. A nucleotide or nucleic acid according to claim 1 wherein M is an enzyme which catalyzes a reaction resulting in the loss or formation of a chromogenic product; a fluorescer having at least one fluorophore; or a molecule capable of specifically binding to another molecule to which a detectable molecule is bound.

7. A nucleotide or nucleic acid according to claim 6, wherein said enzyme is microperoxidase or alkaline phosphatase.

8. A nucleotide or nucleic acid according to claim 6, wherein said fluorescer is fluorescein.

9. A nucleotide or nucleic acid according to claim 6, wherein said specifically binding molecule is biotin.

10. A nucleotide or nucleic acid according to claim 1, wherein M is a synthetic polymer comprising a plurality of groups capable of directly or indirectly producing a detectable signal.

11. A method according to claim 2, wherein at least said synthesizing is carried out on a solid support.

12. A method according to claim 2, wherein said detectable label comprises a macromolecule to which the groups capable of being detected either directly or indirectly are bonded prior to or after reacting with $R_1$.

13. A compound according to claim 3, wherein $R_2$ is a cyanoethyldiisopropylphosphoramidite group.

14. A compound according to claim 3, wherein L is of the formula

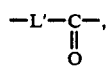

where L' is a diaminated residue and $R_1$ is a diphenylisopropyloxycarbonyl group.

15. An intermediate compound according to claim 14 of the formula:

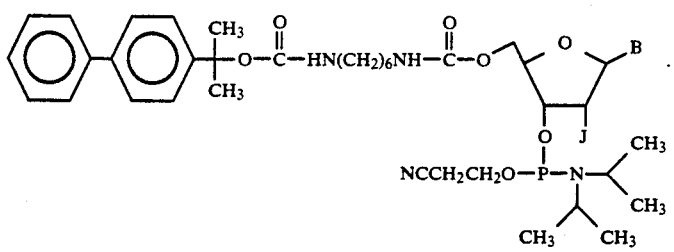

16. A process according to claim 4, wherein

the selective activation of the 5'—OH is with a carbonyldiimidazole, the coupling reaction is with the diaminated residue singly protected on a terminal amine, wherein $R_1$ is a di-phenylisopropyloxycarbonyl group.

17. A process according to claim 4, wherein said 3'—OH is protected with a dimethyl-tert-butylsilyl group.

18. A process according to claim 17, wherein said deprotection employs tetrabutylammonium fluoride.

19. A process according to claim 4, wherein said 3'—OH position is phosphorylated with diisopropylaminocyanoethoxychlorophosphine.

20. A process according to claim 4, wherein said nucleoside is selectively protected at the 5'—OH with an acid labile group; the 3'—OH is protected with a mild or neutral condition liable group; and said selective activation of said 5'—OH is by treatment under mild acid conditions.

21. A process according to claim 20, wherein said acid labile group is dimethoxytrityl and said mild or neutral condition labile group is dimethyl-tert-butylsilyl.

* * * * *